(12) United States Patent
Murata et al.

(10) Patent No.: US 8,752,777 B2
(45) Date of Patent: Jun. 17, 2014

(54) METHOD AND PULVERIZING APPARATUS FOR PREPARING PULVERIZED PRODUCT OF EXTRACTED TOOTH, DEMINERALIZED POWDER ORIGINATED FROM EXTRACTED TOOTH, AND COMPOSITE OF DEMINERALIZED POWDER AND APATITE, SUITABLE FOR USE IN HIGHLY ADVANCED MEDICAL TREATMENTS

(75) Inventors: Masaru Murata, Ishikari-gun (JP); Toshiyuki Akazawa, Sapporo (JP); Katsuo Nakamura, Sapporo (JP); Minoru Arai, Yokohama (JP); Yuto Onodera, Yokohama (JP); Takashi Saito, Ishikari-gun (JP)

(73) Assignees: Health Sciences University of Hokkaido, Tobetsu-Cho (JP); Hokkaido Prefecture, Sapporo-Shi (JP); Mutoh Co., Ltd., Sapporo-Shi (JP)

( * ) Notice: Subject to any disclaimer, the term of this patent is extended or adjusted under 35 U.S.C. 154(b) by 743 days.

(21) Appl. No.: 12/278,359

(22) PCT Filed: Feb. 22, 2007

(86) PCT No.: PCT/JP2007/053321
§ 371 (c)(1),
(2), (4) Date: Aug. 5, 2008

(87) PCT Pub. No.: WO2007/099861
PCT Pub. Date: Sep. 7, 2007

(65) Prior Publication Data
US 2009/0176184 A1   Jul. 9, 2009

(30) Foreign Application Priority Data

Feb. 24, 2006 (JP) .................................. 2006-048476

(51) Int. Cl.
*B02C 19/00* (2006.01)
(52) U.S. Cl.
USPC .......................................................... 241/23

(58) Field of Classification Search
USPC ............................ 241/23, 65, 199.12
See application file for complete search history.

(56) References Cited

U.S. PATENT DOCUMENTS 4,971,261 A * 11/1990 Solomons ........................ 241/99
5,065,946 A * 11/1991 Nishida et al. .................. 241/16
(Continued)

FOREIGN PATENT DOCUMENTS

| JP | 6-72767 | 3/1994 |
| JP | 8-243422 | 9/1996 |

(Continued)

OTHER PUBLICATIONS

Murata et al., "Bone and cartilage induction in nude mice by human demineralized dentin matrix", Journal of Hard Tissue Biology vol. 11(3), pp. 110-114, Mar. 2003, Japan (English abstract included).

(Continued)

*Primary Examiner* — Mark Rosenbaum
(74) *Attorney, Agent, or Firm* — Ditthavong Mori & Steiner, P.C.

(57) ABSTRACT

[Problems] To provide a means and method for providing a pulverized extracted tooth product without causing the extracted teeth to lose their original properties. To provide a new material, originated from the pulverized extracted tooth product and imbued with new properties suited to the regeneration and the like of the alveolar bone.
[Solving means] A method for preparing a pulverized product of extracted tooth, comprising the pulverizing of extracted tooth with a pulverizing apparatus to obtain a pulverized product of an extracted tooth. The pulverizing apparatus comprises a sealable pulverizing chamber and freely rotating pulverizing blade within said pulverizing chamber, and the extracted tooth are pulverized by said pulverizing apparatus together with pieces of physiological saline ice. A method of preparing a demineralized powder originated from an extracted tooth by means of an acid treatment of the pulverized product of extracted tooth obtained by the above method to obtain a demineralized powder. A method of preparing a composite of demineralized powder and apatite by coating the demineralized powder obtained by the above method.

10 Claims, 11 Drawing Sheets

(56) References Cited

U.S. PATENT DOCUMENTS 5,397,068 A * 3/1995 Solomons et al. ............ 241/100
5,769,336 A * 6/1998 Emmerson ...................... 241/36

FOREIGN PATENT DOCUMENTS

| | | |
|---|---|---|
| JP | 09-308640 | 12/1997 |
| JP | 2003-47878 | 2/2003 |
| JP | 2003-320014 | 11/2003 |
| JP | 2005-130730 | 5/2005 |
| WO | 2004-075939 | 9/2004 |

OTHER PUBLICATIONS

Sato et al., "Bone Induction by Human Demineralized Dentin Matrix/Recombinant Human BMP-2 Complex Implant", Dec. 31, 2002, pp. 403-411, vol. 15, No. 4.
Japanese Office Action for corresponding JP Application No. 2006-048476, Dec. 27, 2011.
English translation of the International Preliminary Report on Patentability issued by the International Bureau for the International application No. PCT/JP2007/053321, Sep. 4, 2008.

* cited by examiner

Fig. 1 a) Vessel  b) Blades

ZrO2 ceramics

Mixed powder of enamel and dentin

Variation of concentrations of demineralization samples by electron probe microanalysis (EPMA)

\* : Human demineralized dentin granule        10 μm

Fig. 21

↑ : Induced bone
* : Human demineralized dentin granule

METHOD AND PULVERIZING APPARATUS FOR PREPARING PULVERIZED PRODUCT OF EXTRACTED TOOTH, DEMINERALIZED POWDER ORIGINATED FROM EXTRACTED TOOTH, AND COMPOSITE OF DEMINERALIZED POWDER AND APATITE, SUITABLE FOR USE IN HIGHLY ADVANCED MEDICAL TREATMENTS

TECHNICAL FIELD

The present invention relates to a method for preparing a pulverized product of extracted tooth, a method for preparing a demineralized power originated from extracted tooth, and a method and pulverizing apparatus for preparing a composite of demineralized powder and apatite. The demineralized powder originated from extracted tooth and the composite of demineralized powder and apatite which are obtained by the methods of the present invention can be applied for highly advanced medical treatments.

BACKGROUND ART

Among methods for treating teeth, there are about two million patients who require regeneration of the alveolar bone. There is a great need for the dissemination of a safe, convenient treatment method. Current treatments exist in the form of a method of collecting and embedding bone from the pelvis of the patient, and a recently developed method of using bone marrow cells collecting and cultivating from the patient. However, both of these methods present drawbacks in the areas of patient safety, cost, and the like.

Teeth are comprised of enamel (the outer layer portion of a tooth), dentin, dental pulp, cementum, and periodontal ligament. Most regions are comprised of enamel and dentin. The enamel is comprised of 95 percent apatite (calcium phosphate) and 5 percent water. The dentin is comprised of 70 percent apatite, 20 percent collagen, and 10 percent water. The dentin is known to contain trace quantities of useful proteins and the like for stimulating osteoinduction.

Accordingly, the present inventors considered that teeth that are unneeded by the patient's own (extracted teeth) could be recycled. As an example, they developed a method by which such teeth were pulverized, the granular pulverized product was embedded, and the alveolar bone was regenerated. The present inventors have reported the use of a commercially available manual device to pulverize extracted teeth, the obtaining of samples by demineralizing and washing with hydrochloric acid, and the embedding samples beneath the subcutaneous tissues of the back region in rats and nude mice, resulting in osteoinduction and cartilage induction. (1) Daisuke SATO, Masaru MURATA, Tomoya SASAKI, Toshiyuki AKAZAWA, Makoto ARISUE, Osteoinduction by human demineralized dentin/recombinant human BMP-2 composite implant, *Journal of the Japanese Society of Oral Implantology*, 15, 403-411 (2002) (Nonpatent Reference 1). (2) Masaru MURATA, Daisuke SATO, Toshiyuki AKAZAWA, Toshio TAIRA, Tomoya SASAKI, Makoto ARISUE, Osteoinduction and cartilage induction by human demineralized dentin granules in nude mice, *Journal of Hard Tissue Biology*, 11 (3), 110-114 (2004) (Nonpatent Reference 2). Further, the present inventors have already achieved treatment results in eight patients using this method. Recently, extracted teeth have been placed in frozen storage (for example, in a tooth bank) and later transplanted (delayed transplant treatment). However, to-date, there has been almost no use of extracted teeth in regeneration, and no method of placing extracted teeth in a state permitting their use in regeneration has been established.

Japanese Unexamined Patent Publication (KOKAI) Heisei No. 9-308640 (Patent Reference 1) discloses the use of at least a portion of the root portion of an extracted tooth as a mold to produce an artificial root. However, it does not describe the use of the extracted tooth itself in regeneration.

[Nonpatent Reference 1] Daisuke SATO, Masaru MURATA, Tomoya SASAKI, Toshiyuki AKAZAWA, Makoto ARISUE, Osteoinduction by human demineralized dentin/recombinant human BMP-2 composite implant, *Journal of the Japanese Society of Oral Implantology*, 15, 403-411 (2002).

[Nonpatent Reference 2] Masaru MURATA, Daisuke SATO, Toshiyuki AKAZAWA, Toshio TAIRA, Tomoya SASAKI, Makoto ARISUE, Osteoinduction and cartilage induction by human demineralized dentin granules in nude mice, *Journal of Hard Tissue Biology*, 11 (3), 110-114 (2004).

[Patent Reference 1] Japanese Unexamined Patent Publication (KOKAI) Heisei No. 9-308640.

Problems to be Solved by the Invention

As set forth above, the present inventors have developed a method of regenerating the alveolar bone by pulverizing extracted teeth and embedding the granular pulverized product. However, the pulverizing of extracted teeth is conducted manually with a mortar. To render this method more general, a means or method is required for providing powder having a particle diameter suited to embedding so that the chemical components and properties such as the calcification promoting ability, which are originally contained in extracted teeth are not lost.

Further, not just the simple pulverization of extracted teeth, but the providing of a new material that is originated from the pulverized extracted tooth product, imbued with new properties such as the activation of bone forming cells, and suited to the regeneration of the alveolar bone is needed.

Accordingly, the first object of the present invention is to provide a means and method for providing a pulverized extracted tooth product without causing the extracted teeth to lose their original properties.

The second object of the present invention is to provide a new material, originated from the pulverized extracted tooth product and imbued with new properties suited to the regeneration and the like of the alveolar bone.

Means for Solving the Problems

The present invention is configured to achieve both of the above-stated objects as follows.

[1] A method for preparing a pulverized product of an extracted tooth, comprising the pulverizing of extracted tooth with a pulverizing apparatus to obtain a pulverized product of an extracted tooth, characterized in that:

said pulverizing apparatus comprises a sealable pulverizing chamber and freely rotating pulverizing blade within said pulverizing chamber, and said extracted tooth are pulverized by said pulverizing apparatus together with pieces of physiological saline ice.

[2] The method of [1] wherein at least the inner wall and pulverizing blade of said pulverizing chamber are comprised of zirconia.

[3] The method of [1] or [2] wherein the rotational speed of said pulverizing blade falls within a range of 10,000 to 15,000 rpm.

[4] The method of any one of [1] to [3] wherein each of said pieces of physiological saline ice has a volume falling within a range of 0.5 to 8 cm$^3$.

[5] The method of any one of [1] to [4] wherein a single extracted tooth is pulverized in a single pulverizing cycle.

[6] The method of any one of [1] to [5] wherein a total quantity of pieces of physiological saline ice falling within a range of 10 to 40 cm$^3$ is employed for a single extracted tooth.

[7] The method of any one of [1] to [6] wherein the pulverization period is selected so that the particle size of the pulverized product of extracted tooth falls within a range of 0.1 to 2.0 mm.

[8] The method of any one of [1] to [7] wherein an extracted tooth is pulverized as is to obtain a pulverized product of extracted tooth in the form of a mixture of enamel and dentin.

[9] The method of any one of [1] to [7] wherein the outer surface of said extracted tooth is eliminated prior to pulverizing to obtain a pulverized product of an extracted tooth that is dentin.

[10] A method of preparing a demineralized powder originated from an extracted tooth, comprising the demineralization by means of an acid treatment of the pulverized product of extracted tooth obtained by the method described in any one of [1] to [9] to obtain a demineralized powder.

[11] The method of [10], wherein said acid treatment is conducted with an aqueous solution of a strong acid.

[12] The method of [10] or [11] wherein said acid treatment is conducted with said pulverizing apparatus.

[13] The method of any one of [10] to [12] wherein said demineralized powder comprises collagen and bone morphogenetic protein.

ADVANTAGES OF THE INVENTION

The present invention permits the ready preparation of a pulverized extracted tooth product that can be employed in various dental treatments. It is also possible to prepare demineralized powder originated from extracted tooth, and a composite of demineralized powder and apatite, from the pulverized extracted tooth product. The present invention also provides a pulverizing apparatus suited to use in preparing the pulverized extracted tooth product, demineralized powder, and composite of demineralized powder and apatite.

BEST MODE OF IMPLEMENTING THE INVENTION

The Method for Preparing a Pulverized Extracted Tooth Product

The method for preparing a pulverized extracted tooth product of the present invention comprises the pulverizing of extracted tooth with a pulverizing apparatus to obtain a pulverized extracted tooth product. This preparation method is characterized by the use of a pulverizing apparatus having a sealable pulverizing chamber and freely rotating pulverizing blade within said pulverizing chamber, and in that extracted tooth are pulverized by the pulverizing apparatus together with pieces of physiological saline ice.

[The Pulverizing Apparatus]

The pulverizing apparatus employed in the present invention will be described first.

The pulverizing apparatus employed in the present invention comprises a sealable pulverizing chamber and freely rotating pulverizing blade within the pulverizing chamber. At least the inner walls and pulverizing blade of the pulverizing chamber are desirably comprised of zirconia ($ZrO_2$). The reason why it is desirable for at least the inner walls and pulverizing blade of the pulverizing chamber to be comprised of $ZrO_2$ is that $ZrO_2$ is bio-inert and is a material that can be applied to biomaterials; thus, it would not be medically problematic even if abrasion powder from the inner walls or pulverizing blade were mixed into the pulverized powder of an extracted tooth during pulverizing. Further, $ZrO_2$ has good resistance to heat, good resistance to abrasion, and good chemical durability, affording the advantages of permitting heat sterilization, other forms of sterilization, and treatment with strong acids and alkalis.

The pulverizing apparatus will be described through a specific example. The pulverizing vessel, for example, may be a pulverizing chamber in the form of a cylindrical vessel (for example, 7.2 cm in diameter and 5.6 cm in height), with a $ZrO_2$ film having been applied by thermal plasma spraying on parts that are difficult to process as $ZrO_2$ sintered bodies. A lid is provided on the vessel to render the pulverizing chamber sealable. The lid may be made of $ZrO_2$, or $ZrO_2$ may be applied by thermal plasma spraying to the side of the lid facing the inside of the vessel. A freely rotating pulverizing blade is provided within the vessel. The pulverizing blade is made of $ZrO_2$. The pulverizing blade may be in the form of a thick rectangle (60×15.5×8.5 mm), in the form of a thin rectangle (64×12.3×6.3 mm), in the form of a thick rhombus (60×15.5×9 mm), or the like. For example, the pulverizing blade may extend from the bottom of the vessel and be fixed at the other end to one end of a rotating shaft that is linked by a driving means to a motor or the like for rotation.

The pulverizing blade desirably rotates at a speed of 10,000 to 15,000 rpm during preparation of the pulverized extracted tooth product. A driving means such as a motor that is capable of rotating at such speeds is thus employed. Further, since the pulverizing apparatus is employed in cleaning or demineralization treatment in addition to the preparation of the pulverized extracted tooth product, a driving means in the form of a motor or the like that is also capable of rotating at a range of 1,000 to 10,000 rpm is desirably employed.

In the method for preparing a pulverized extracted tooth product of the present invention, the above pulverizing apparatus is employed and the extracted tooth are pulverized by the pulverizing apparatus together with pieces of physiological saline ice. The extracted tooth are pulverized to a desired particle size falling within a range of 0.1 to 2.0 mm, for example. This is desirable from the perspective of use in treatments such as generating bone or the like in areas where bone is lacking due to periodontal disease or the like, teeth transplants, and the establishment of implants. The rotational speed of the pulverizing blade desirably falls within a range of 10,000 to 15,000 rpm to rapidly pulverize the extracted tooth to the above-stated particle size. However, when the pulverizing blade is rotated at such a high speed, the temperature of the extracted tooth rises during pulverization. Osteoinductive proteins such as bone morphogenetic protein (BMP), calcification-promoting substances such as phosphophorin, and the like are contained in the pulverized dentin product of extracted tooth. In the course of pulverization, these physiologically active substances are denatured by heat. Thus, this temperature increase is undesirable from the perspective of using the pulverized product in the above-described medical treatments. Accordingly, extracted tooth are pulverized together with pieces of physiological saline ice in the present invention.

From the perspective of obtaining a pulverized product of desired particle size, the volume of each piece of physiological saline ice desirably falls within a range of 0.5 to 8 $cm^3$. From a similar perspective, a single extracted tooth is desirably pulverized per pulverization cycle, and for each extracted tooth, the total quantity of pieces of physiological saline ice employed desirably falls within a range of 10 to 40 $cm^3$. From the perspective of obtaining a pulverized product of desired particle size, the pieces of physiological saline ice are desirably spherical or nearly spherical in shape, as opposed to being square. When employing square pieces of physiological saline ice, it is desirable to place them at room temperature or the like for a certain period so that their corners melt, causing them to become rounded. It is also possible to make and employ spherical, or nearly spherical, pieces of physiological saline ice from the start.

The duration of pulverization can be suitably selected to yield a pulverized extracted tooth product with a particle size falling within a range of 0.1 to 2.0 mm, as set forth above.

Following extraction, the extracted tooth can be washed as needed and then employed as is in pulverization. In that case, a pulverized extracted tooth product comprised of a mixture of enamel and dentin will be obtained. Alternatively, the extracted tooth can be washed as needed following extraction, after which part or all of the outer surface can be eliminated (by grinding, for example) prior to pulverization. In that case, a pulverized extracted tooth product comprised of dentin will be obtained. Accordingly, whether or not the outer surface of the extracted tooth is eliminated can be suitably determined based on the use to which the pulverized extracted tooth product is to be put.

Following the completion of pulverization, the pulverized product is separated from the solution and, as needed, washed and/or dried. Separation of the pulverized product from the solution can be conducted, for example, by the steps of suction filtering the pulverized slurry, washing with ultrapure water, and drying at room temperature. At the completion of pulverization, the pieces of physiological saline ice will be nearly melted. However, a portion of the ice will sometimes remain in a state something like sherbet. In such cases, washing with a large quantity of ultrapure water can be conducted at room temperature to completely remove the physiological saline ice. The cleaned and/or dried pulverized product can be employed as is in treatment, or can be stored (at −196° C. to 20° C., for example) until use.

[the Method of Preparing a Demineralized Power Originated from Extracted Tooth]

The present invention includes a method for preparing a demineralized powder originated from extracted tooth. This preparation method comprises obtaining a demineralized powder by subjecting the pulverized extracted tooth product obtained by the above-described method of the present invention to an acid treatment. The acid treatment can be conducted with an aqueous solution of a strong acid. For example, an aqueous solution of nitric acid or an aqueous solution of hydrochloric acid may be employed as the aqueous solution of a strong acid. The concentration of the aqueous solution of nitric acid or hydrochloric acid can be suitably determined taking into account the quantity that must be added to partially or completely dissolve the apatite component originated from the extracted tooth. For example, a commercially available nitric acid or hydrochloric acid reagent can be diluted 5 to 10-fold in ultrapure water to obtain a 10 to 20 percent nitric acid or hydrochloric acid aqueous solution.

The acid treatment can be conducted using 10 to 50 mL of the above aqueous solution per 0.1 g of pulverized extracted tooth product, for example. The acid treatment can be conducted for 1 to 10 hours at room temperature, for example. As needed, the acid treatment can be conducted with cooling. The conditions of the acid treatment (acid concentration, temperature, duration, ratio to the acid aqueous solution, and the like) can be suitably determined taking into account the physical properties and composition of the demineralized powder obtained by demineralization with the acid treatment.

The acid treatment can be conducted with the above-described pulverizing apparatus. Since the inner walls and pulverizing blade of the above-described pulverizing apparatus are made of zirconia, it is highly durable with respect to the above-described acid aqueous solutions. When employing the above pulverizing apparatus, a rotational speed of the pulverizing blade falling within a range of 1,000 to 5,000 rpm, for example, is suitable. Following treatment with the acid aqueous solution, the demineralized powder is separated from the acid aqueous solution and, as needed, washed and/or dried. The demineralized powder obtained can be employed as is in treatment, or can be stored (at −196° C. to 20° C., for example) until use.

The demineralized powder obtained by the above-described demineralization contains collagen and bone morphogenetic protein. However, the composition of the demineralized powder will vary as set forth below depending on whether part or all of the outer surface of the extracted tooth serving as starting material for the pulverized product has been eliminated, or an intact extracted tooth is employed. For completely demineralized dentin, the composition will be 95 percent collagen and 5 percent water, while for partially demineralized dentin, it will be 0 to 70 percent apatite, 20 to 95 percent collagen, and 5 to 10 percent water.

The demineralized powder obtained by the method of the present invention can be employed to treat bone that has been damaged by periodontal disease or the like, tooth transplants, and bone generation or the like in and the establishment of implants.

[The Method for Preparing a Composite of Demineralized Powder and Apatite]

The present invention includes a method for preparing a composite of demineralized powder and apatite. The present invention includes the coating and combining of apatite on the outer surface of the demineralized powder obtained by the above-described method of the present invention. It is possible to control the bioabsorption rate and osteoinduction ability of the material at the treatment site by selecting the state and amount of the apatite coating.

To coat apatite, a filtrate obtained by pulverizing an extracted tooth with pieces of physiological saline ice and filtering out the pulverized extracted tooth product may be employed. In the course of preparing the above-described pulverized extracted tooth product, this filtrate is the solution that is separated from the pulverized product after pulverizing and can be employed as is. The filtrate contains calcium and phosphoric acid, which function as the starting materials of apatite.

First, the pH of the filtrate is adjusted to a condition where the apatite precipitates. A "condition where the apatite precipitates" means, for example, a pH ranging from 7 to 8. The pH of the filtrate will normally be on the acidic side, so the pH can be adjusted, for example, by adding an alkaline aqueous solution such as an ammonia aqueous solution.

The solution containing the precipitated apatite and the demineralized powder are then mixed under pH conditions (pH 8 or less) where the protein contained in the demineralized powder will not be denatured. The mixing proportions of the demineralized powder and the solution containing the apatite are suitably set to an apatite range of 0 to 50 percent, for example, by taking into account a bioabsorption rate suited to the treatment site.

After mixing the demineralized powder and the solution containing the apatite, the pH of the solution can then be adjusted to a condition under which the apatite ages to disperse the apatite in the demineralized powder and have a composite. The pH can be adjusted in the manner set for above, for example, by adding an alkaline aqueous solution such as an ammonia aqueous solution. The conditions for aging the apatite are identical to those set forth above.

Alternatively, after apatite has been precipitated at pH 9 to 11 in the initial pH adjustment, filtered, washed, the separated apatite can be mixed with the demineralized powder. The pH of the mixture can then be adjusted to a condition under which the apatite ages to disperse the apatite in the demineralized powder and have a composite. The pH can be adjusted in the same manner as set forth above, for example, by adding an alkaline aqueous solution such as an ammonia aqueous solution. The "condition under which the apatite ages" referred to here is pH 7 to 8.

The above coating of and combining with the apatite can be conducted at room temperature, or can be conducted as needed with cooling. The above coating of and combining with the apatite can be conducted with the above-described pulverizing apparatus. When conducted with the above pulverizing apparatus, the rotational speed of the pulverizing blade suitably falls within a range of 500 to 3,000 rpm, for example.

The apatite-coated and combined demineralized powder is immersed in a simulated body fluid (SBF) near the biomimetic environment. The period of immersion can be suitably selected to control the crystal growth of the HAp solid solution containing ions derived from the SBF and construct cocoon or sea urchin like-porous surfaces. In this manner, the material prepared by immersion in the SBF will be a biomaterial with surface nature that can be designed and controlled.

The pulverized powder of the extracted tooth, the demineralized powder originated from extracted tooth, and the composite of demineralized powder and apatite of the present invention can be used as a transplant material or the like in the course of dental treatment such as the treatment of periodontal disease. In addition to being used singly as a transplant material, such an extracted tooth pulverized powder, demineralized powder originated from extracted tooth, or composite of demineralized powder and apatite can be transplanted by adding dental pulp tissue from the patient's own body, depending on the case. Dental pulp is comprised of hard tissue-forming cells. Since bone morphogenetic protein (BMP) that induces bone in tissue is present in such tissue, osteogenesis can be promoted more rapidly than with pulverized extracted tooth product alone when dental pulp tissue is added to the pulverized extracted tooth product.

EMBODIMENTS

The present invention will be described in greater below through embodiments.

The Pulverizing Apparatus

Figure 1:
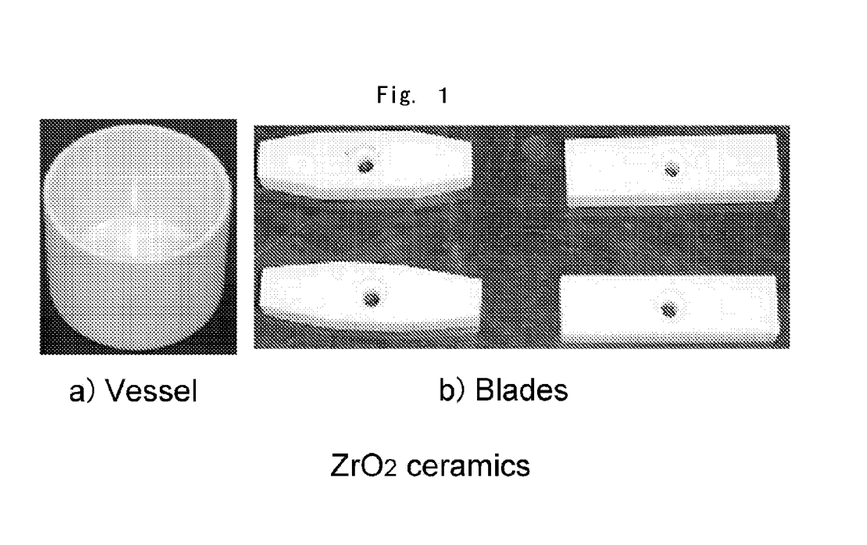
FIG. 1 Photographs of a zirconia vessel and a zirconia pulverizing blades.
Figure 2:
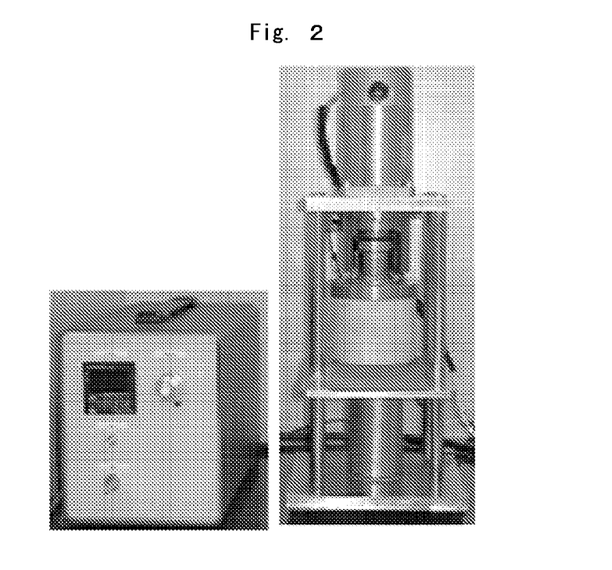
FIG. 2 A photograph of a pulverizing apparatus (recycling unit for teeth).
Figure 3:
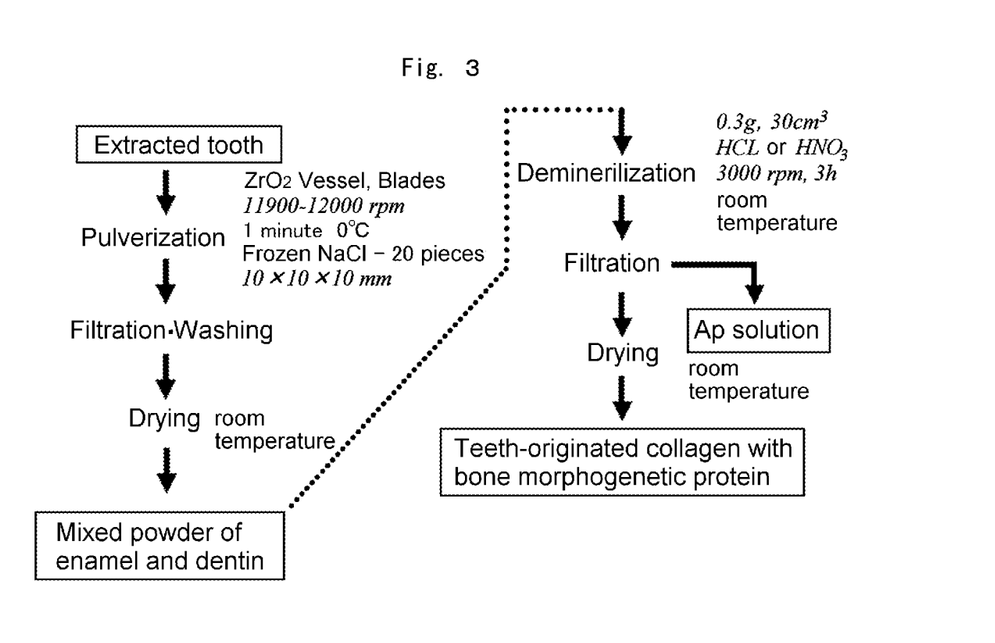
FIG. 3 Schematic of a method for preparing TOC-BMP (teeth-originated collagen with bone morphogenetic protein) in Embodiment 2.

The pulverizing apparatus (recycling unit for teeth) shown in FIG. 2 was employed with the zirconia ($ZrO_2$) vessel, $ZrO_2$ pulverizing blades (thick rectangular: 60×15.5×8.5 mm; thin rectangular: 64×12.3×6.3 mm, thick rhomboid: 60×15.5×9 mm), and pulverizing vessel (7.2 cm in diameter, 5.6 cm in height) shown in FIG. 1. A $ZrO_2$ thermal spray film was applied to portions of the $ZrO_2$ vessel that were difficult to process as $ZrO_2$ sintered products.

Embodiment 1

Examination of Extracted Tooth Pulverization Conditions

Physiological saline ice of prescribed size (10×10×10 mm, 15×15×15 cm, 20×20×20 mm) was charged to the $ZrO_2$ vessel to prevent exothermic phenomenon of the extracted tooth and clean them. Three types of $ZrO_2$ pulverizing blades (thick rectangular, thin rectangular, and thick rhomboid) were employed to pulverize a single extracted tooth at high speed under conditions of 11,900 to 12,000 rpm for one minute. In all cases, residual physiological saline ice was observed, and the interior of the vessel was maintained at 0° C., and pulverized products of various particle sizes were obtained. Physiological saline ice that had been left standing at −80° C. for one day and then placed at room temperature for about 5 minutes so that it started melting to round off the corners of the cubes was employed in order to prevent the pulverized product from cling to the tops of the inner walls of the vessel. The particle size of the pulverized extracted tooth product did not vary with the type of $ZrO_2$ pulverizing blade, but did vary with the size of the physiological saline ice and the amounts of packed ice. As the size of the physiological saline ice increased, a tendency of the particle size of the pulverized product to increase was observed.

Embodiment 2

Preparation of Pulverized Product of Extracted Tooth

Figure 4:
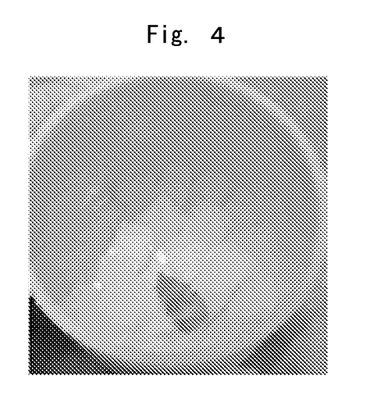
FIG. 4 A photograph showing an extracted tooth prior to pulverization in Embodiment 2.
Figure 5:
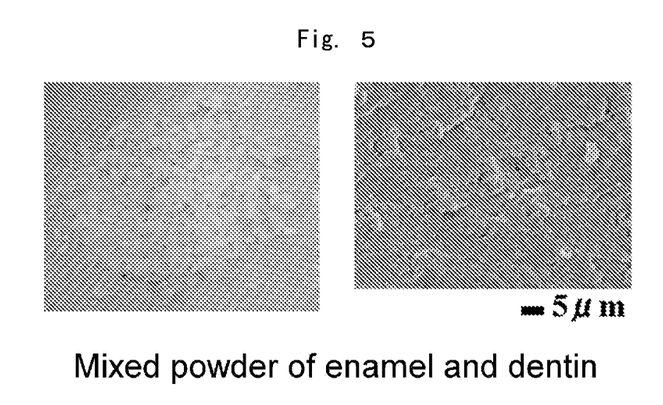
FIG. 5 Photographs showing the pulverized product obtained in Embodiment 2.

Based on the results of the examination in Embodiment 1, a pulverized product of an extracted tooth was prepared under the following conditions. To a $ZrO_2$ vessel were charged 20 pieces of physiological saline ice measuring 10×10×10 mm. A single extracted tooth was then added. A thick rhomboid $ZrO_2$ pulverizing blade was employed to pulverize the mixture at high speed under conditions of 11,900 to 12,000 rpm for one minute. The pulverized slurry containing the physiological saline ice was filtered to remove impurities such as gingiva, after which the filtrate was washed with 100 cm$^3$ of ultrapure water and dried for 24 hours at room temperature, yielding a pulverized sample (a mixed powder of enamel and dentin) with a particle size of 0.5 to 1 mm that was ideal for regenerating alveolar bone. FIG. 4 shows the extracted tooth prior to pulverization and FIG. 5 shows photographs of the pulverized product.

Embodiment 3

The Processing Step of Demineralizing a Pulverized Sample of Extracted Tooth

Figure 6:
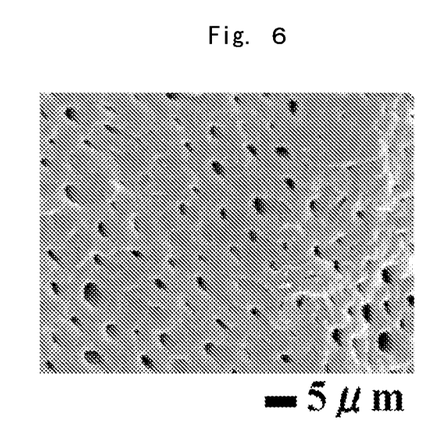
FIG. 6 A photograph showing the demineralized powder obtained using HCl aqueous solution in Embodiment 3.
Figure 7:
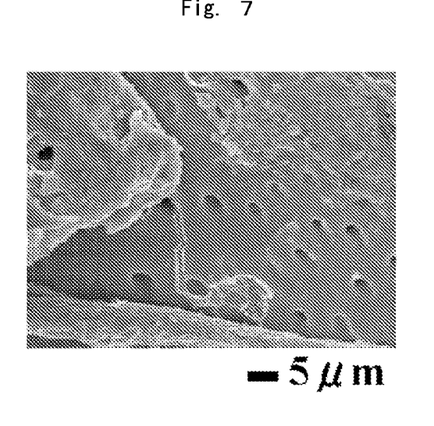
FIG. 7 A photograph showing the demineralized powder obtained using HNO$_3$ aqueous solution in Embodiment 3.

To a $ZrO_2$ vessel, 0.3 g of the mixed powder of enamel and dentin obtained in Embodiment 2 and 30 cm$^3$ of 2 percent HCl or $HNO_3$ aqueous solution were charged. The mixture was demineralized by stirring with a $ZrO_2$ pulverizing blade for three hours at 3,000 rpm to obtain a demineralized powder out of which the mineral components had been completely dissolved. FIG. 6 shows a photograph of the demineralized powder obtained using HCl aqueous solution. FIG. 7 shows a photograph of the demineralized powder obtained using $HNO_3$ aqueous solution.

Figure 8:
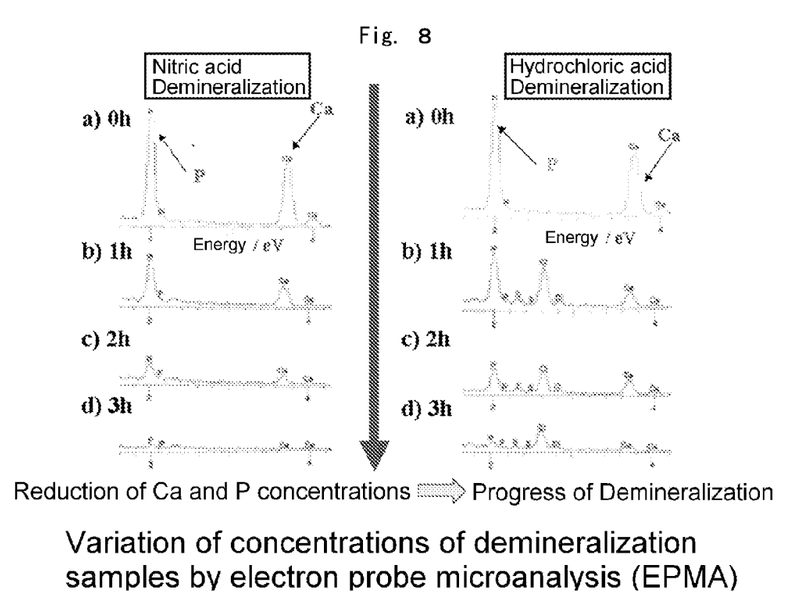
FIG. 8 Results of electron probe microanalysis (EPMA) of the demineralized powder obtained in Embodiment 3.

Electron probe microanalysis (EPMA) of the demineralized powder obtained revealed that as the duration of the acid treatment increased, the Ca and P concentrations decreased. At about three hours, almost no Ca or P was detected. Thus, the demineralization reaction was determined to be nearly complete (FIG. 8).

To keep the temperature within the $ZrO_2$ vessel from exceeding 36° C., it was desirable to ensure cooling for a necessary period by adjusting the amount of acid aqueous solution employed or cooling the outside walls of the vessel. When the vessel temperature rose during the demineralization step, denaturation of collagen and decreased activity of bone morphogenetic protein (BMP) were observed.

The demineralized slurry was filtered, washed with 100 to 150 cm$^3$ of ultrapure water, and dried for 24 hours at room temperature to obtain 0.17 g of teeth-originated collagen with bone morphogenetic protein (TOC-BMP).

Embodiment 4

Figure 9:
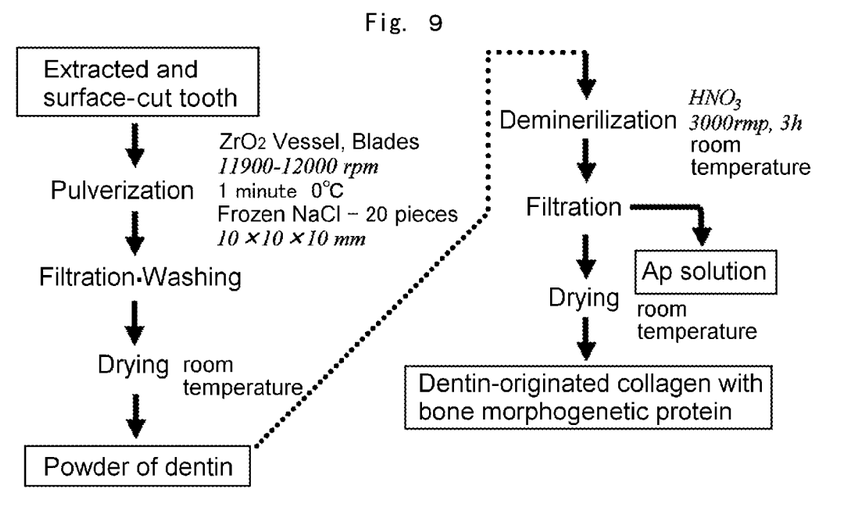
FIG. 9 Schematic of a method for preparing DOC-BMP (dentin-originated collagen with bone morphogenetic protein) in Embodiment 4.
Figure 10:
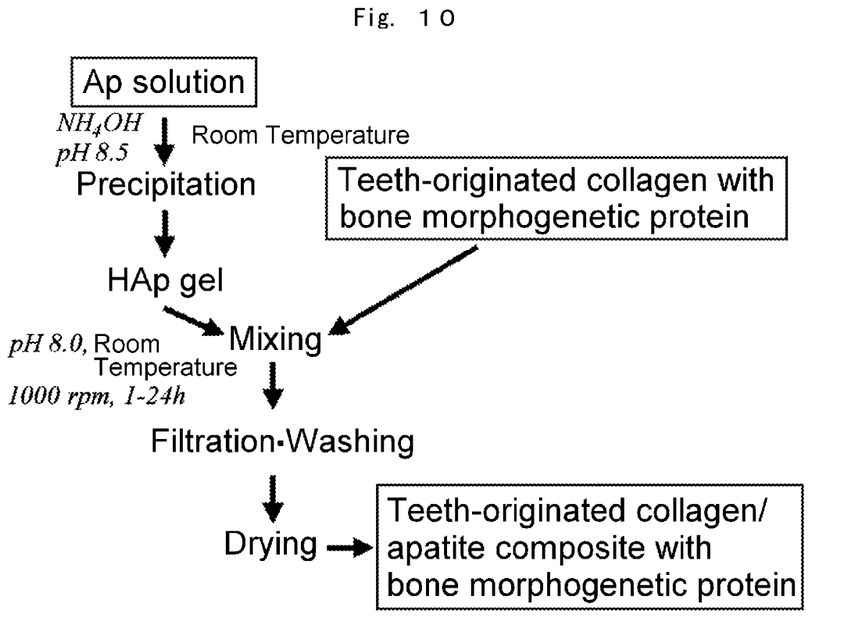
FIG. 10 Schematic of a method for preparing TOC/AC-BMP (teeth-originated collagen/apatite composite with bone morphogenetic protein) (No. 1) in Embodiment 5.

Pulverizing, Washing, and Demineralization Treatment of Extracted and Surface-Cut Tooth Extracted and surface-cut tooth were employed as starting samples under the same conditions as in Embodiments 2 and 3. Since the enamel in the vicinity of the outer surface of the extracted tooth had been removed, 0.11 g of dentin-originated collagen with bone morphogenetic protein (DOC-BMP) was obtained by the same pulverization, washing, and demineralization steps (FIG. 9) as set forth above.

Embodiment 5

Technique for Preparing Apatite/Collagen Composite Material Originated from Extracted Tooth (1)

Preparation of TOC/AC-BMP (No. 1) (Combining of HAp with Collagen Accompanying Crystal Growth)

Figure 11:
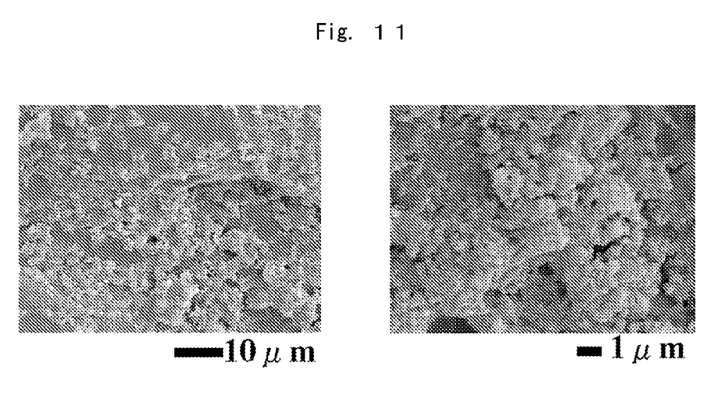
FIG. 11 Photographs showing the microstructure of TOC/AC-BMP (teeth-originated collagen/apatite composite with bone morphogenetic protein) (No. 1) in Embodiment 5.

The a) filtrate of pulverized slurry (Ap) containing physiological saline ice of the demineralization step and b) TOC-BMP powder of the extracted tooth pulverized sample in Embodiment 3 are employed. The Ap filtrate was charged to the $ZrO_2$ vessel, and 3 cm$^3$ of 10 percent $NH_3$ water was added dropwise at room temperature to adjust the pH to about 8.5, and the mixture was stirred for 4 hours at 1,000 rpm to cause the apatite (HAp) to reprecipitate. The TOC-BMP powder was added to this HAp slurry and the mixture was mixed by stirring for 4 hours at 1,000 rpm at about pH 8.0 at room temperature to disperse and combine the HAp crystals on the surface of the TOC-BMP. The product was filtered, washed with 10,000 cm$^3$ of ultrapure water, and dried for 24 hours at room temperature, yielding 0.52 g of a composite material of TOC-BMP and HAp (TOC/AC-BMP (No. 1)). FIG. 11 shows photographs (of the microstructure) of TOC/AC-BMP (No. 1).

Embodiment 6

Technique for Preparing Apatite/Collagen Composite Material Originated from Extracted Tooth (2)

Preparation of DOC/AC-BMP (No. 1) (Combining of HAp with Collagen Accompanying Crystal Growth)

Figure 12:
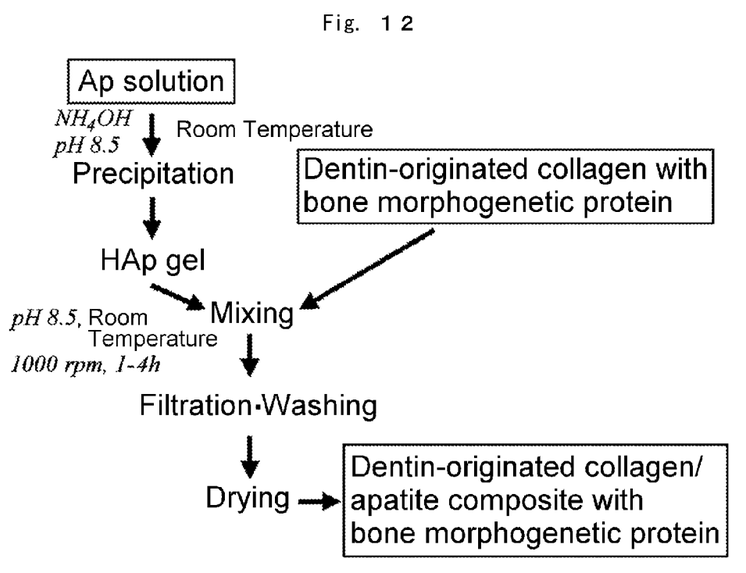
FIG. 12 Schematic of a method for preparing DOC/AC-BMP (dentin-originated collagen/apatite composite with bone morphogenetic protein) (No. 1) in Embodiment 6.
Figure 13:
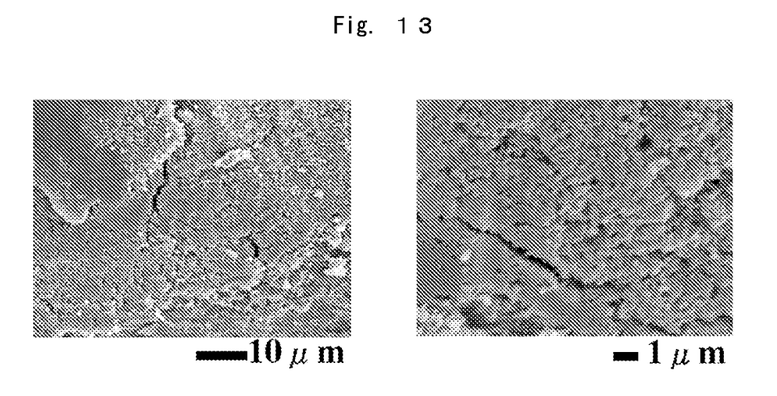
FIG. 13 Photographs showing the microstructure of DOC/AC-BMP (dentin-originated collagen/apatite composite with bone morphogenetic protein) (No. 1) in Embodiment 6.

The a) Ap filtrate in the demineralization step and the b) DOC-BMP powder when employing extracted and surface-cut tooth in Embodiment 4 are employed. A 0.50 g quantity of a composite material (DOC/AC-BMP (No. 1)) of DOC-BMP and HAp was obtained by the same steps as in Embodiment 5. FIG. 12 shows a schematic of the method of preparing DOC/AC-BMP (No. 1), and FIG. 13 shows photographs (of the microstructure) of the DOC/AC-BMP (No. 1) obtained.

Embodiment 7

Technique for Preparing Apatite/Collagen Composite Material Originated from Extracted Tooth (3)

Preparation of TOC/AC-BMP (No. 2) (Combining of HAp Gel with Collagen)

Figure 14:
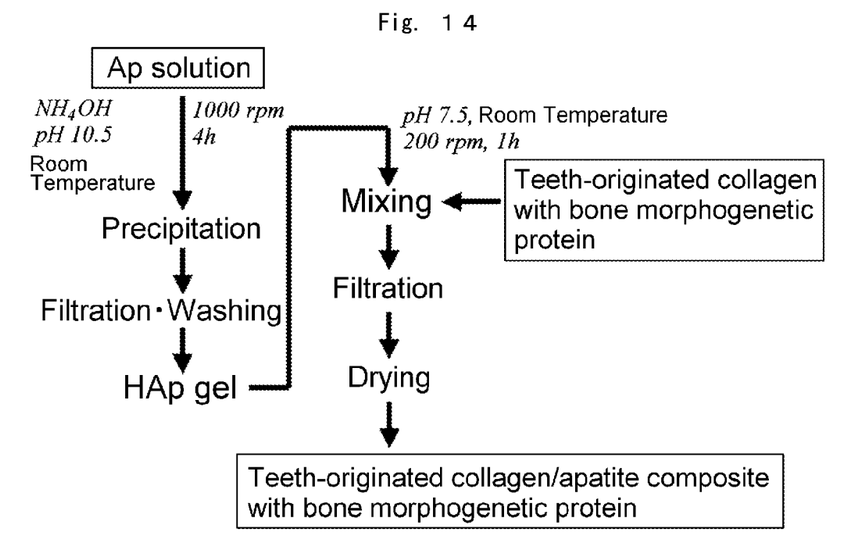
FIG. 14 Schematic of a method for preparing TOC/AC-BMP (teeth-originated collagen/apatite composite with bone morphogenetic protein) (No. 2) in Embodiment 7.
Figure 15:
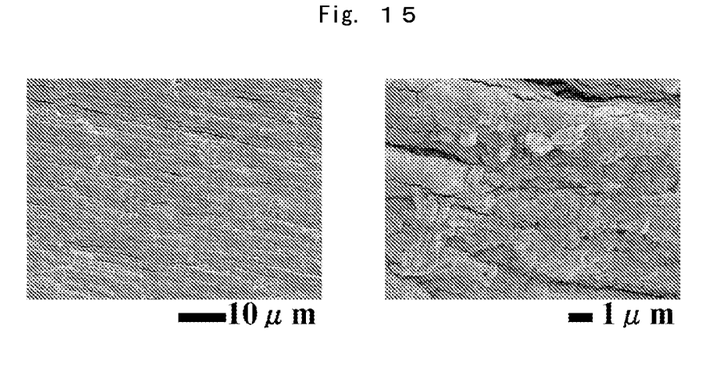
FIG. 15 Photographs showing the microstructure of TOC/AC-BMP (teeth-originated collagen/apatite composite with bone morphogenetic protein) (No. 2) in Embodiment 7.

The a) Ap filtrate during the demineralization step and the b) TOC-BMP powder of the extracted tooth pulverized sample of Embodiment 3 are employed. While stirring the Ap filtrate at 1,000 rpm at room temperature, 200 cm³ of 10 percent NH₃ water was added dropwise over one hour to adjust the pH to 10.5. The mixture was then aged by stirring for 3 hours to cause the apatite (HAp) to reprecipitate. This was filtered and washed with 18,000 cm³ of ultrapure water to prepare an HAp gel at pH 7.5 or lower. To 50 cm³ of the HAp gel slurry was added TOC-BMP powder and mixing was conducted by stirring for 1 hour at 200 rpm at room temperature to disperse and combine the HAp crystals on the surface of the TOC-BMP. This product was dried for 24 hours at room temperature, yielding 0.45 g of TOC/AC-BMP (No. 2). FIG. 14 shows a schematic of the method of preparing TOC/AC-BMP (No. 2), and FIG. 15 shows photographs (of the microstructure) of the DOC/AC-BMP (No. 2) obtained.

Embodiment 8

Technique for Preparing Apatite/Collagen Composite Material Originated from Extracted Tooth (4)

Preparation of DOC/AC-BMP (No. 2) (Combining of HAp Gel with Collagen)

Figure 16:
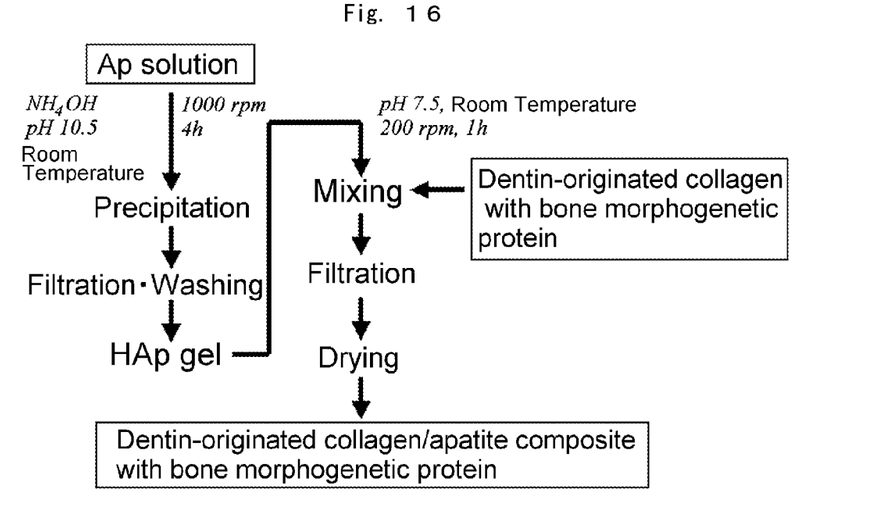
FIG. 16 Schematic of a method for preparing DOC/AC-BMP (dentin-originated collagen/apatite composite with bone morphogenetic protein) (No. 2) in Embodiment 8.

The a) Ap filtrate during the demineralization step and the b) DOC-BMP powder when employing the extracted and surface-cut tooth of Embodiment 4 are employed. A 0.44 g quantity of DOC/AC-BMP (No. 2) was obtained by the same steps as in Embodiment 7. FIG. 16 shows a schematic of the method of preparing DOC/AC-BMP (No. 2).

Embodiment 9

Technique for Preparing Apatite/Collagen Composite Material Originated from Extracted Tooth (5)

Preparation of TOC/AC-BMP (No. 3) (Surface Modification with HAp Microcrystals in Simulated Body Fluid)

Figure 17:
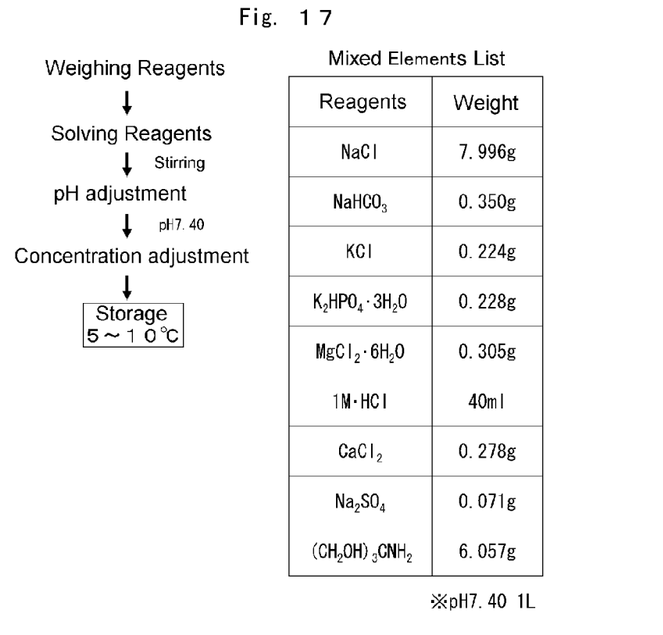
FIG. 17 Schematic showing the method for preparing simulated body fluid and conditions (a table) in Embodiment 9.

Simulated body fluid (SBF) was prepared for the precipitation of HAp microcrystals in a biomimetic environment. About 700 cm³ of ultrapure water and a stirrer were placed in a 1,000 cm³ polyethylene beaker. The beaker was then placed in a thermostatic chamber and maintained at 36.5° C. NaCl, NaHCO₃, KCl, K₂HPO₄.3H₂O, MgCl₂.6H₂O, 1M HCl, CaCl₂, Na₂SO₄, and (CH₂OH)₃CNH₂ reagents were sequentially added while stirring. 1M HCl was gradually added dropwise to adjust the solution to pH 7.40. In a measuring cylinder, ultrapure water was added to make 1,000 cm³, and the mixture was charged to a polyethylene bottle and stored in a refrigerator at 5 to 10° C. FIG. 17 shows a schematic and the conditions (a table) of the method of preparing the biomimetic solution.

Figure 18:
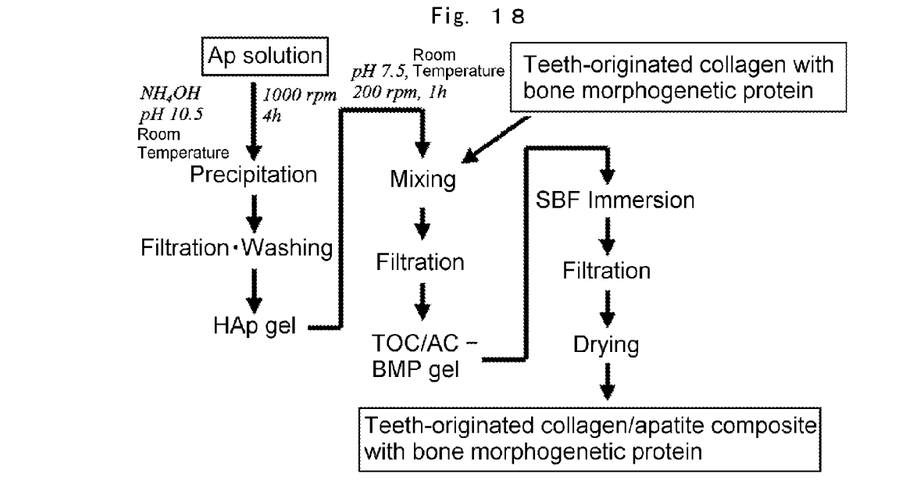
FIG. 18 Schematic of a method for preparing TOC/AC-BMP (teeth-originated collagen/apatite composite with bone morphogenetic protein) (No. 3) in Embodiment 9.

The a) Ap filtrate during the demineralization step and b) TOC-BMP powder of the extracted tooth pulverized sample of Embodiment 3 are employed. While stirring the Ap filtrate at 1,000 rpm at room temperature, 200 cm³ of 10 percent NH₃ water was added dropwise over an hour to adjust the filtrate to pH 10.5. Curing was conducted by stirring for three hours, causing the apatite (HAp) to reprecipitate. This was filtered and washed with 18,000 cm³ of ultrapure water to prepare an HAp gel of pH 7.5 or lower. To 50 cm³ of the HAp gel slurry was added TOC-BMP powder and the components were mixed by stirring for one hour at 200 rpm at room temperature, yielding a TOC/AC-BMP gel comprising HAp crystals dispersed on, and combined with, the surface of the TOC-BMP. This was immersed for 7 days in 100 cm³ of SBF at pH 7.40 and 36.5° C., filtered, and dried, yielding 0.48 g of TOC/AC-BMP (No. 3) with precipitated bone-like apatite. FIG. 18 shows a schematic of the method of preparing TOC/AC-BMP (No. 3).

Embodiment 10

Technique for Preparing Apatite/Collagen Composite Material Originated from Extracted Tooth (6)

Preparation of DOC/AC-BMP (No. 3) (Surface Modification with HAp Microcrystals in Simulated Body Fluid)

Figure 19:
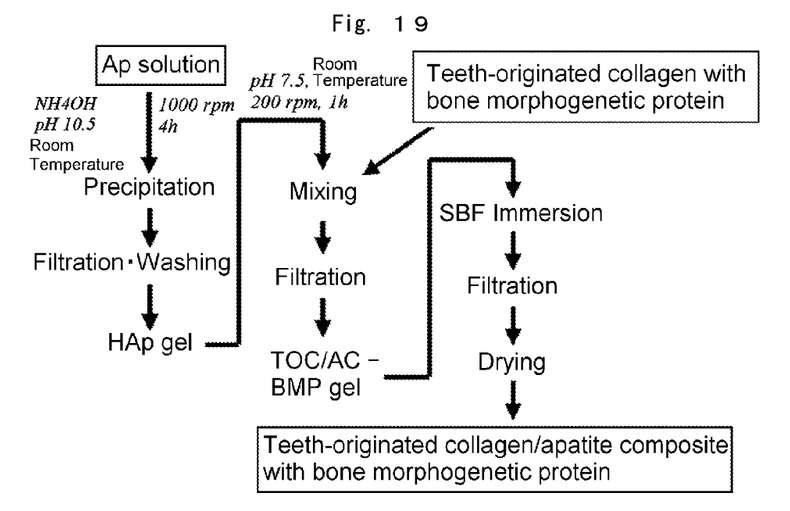
FIG. 19 Schematic of a method for preparing the DOC/AC-BMP (dentin-originated collagen/apatite composite with bone morphogenetic protein) (No. 3) of FIG. 18 in Embodiment 10.

The a) Ap filtrate during the demineralization step and b) DOC-BMP powder when employing the extracted and surface-cut tooth of Embodiment 4 are employed. A 0.47 g quantity of DOC/AC-BMP (No. 3) was obtained by the same steps as in Embodiment 9. FIG. 19 shows a schematic of the method of preparing DOC/AC-BMP (No. 3).

Embodiment 11

1. Laboratory Animals and Rearing

Male, four-week-old nude mice (body weight: about 30 g) were employed as laboratory animals. After a week-long quarantine period, the animals were subjected to fully-body inspections to ensure the absence of anomalies, after which they were subjected to the following test.

2. Preparation of Human Demineralized Dentin

The demineralized dentin granules (TOC-BMP powder) prepared in Embodiment 3 were divided into 70 mg quantities and loaded into improved syringes (1 mL improved injection syringes for tuberculin). Immediately prior to implantation, 100 microliters of physiological saline was added dropwise to the TOC-BMP powder, impregnating it.

3. Subcutaneous Implantation

Under general anesthesia, subcutaneous incisions (roughly 10 mm) were added into two regions, one on each side of the back, and the subcutaneous connective tissue was bluntly separated to form pockets. The materials were implanted into the pockets about 10 mm apart from the incisions so that they would not return to the vicinity of the incisions. After restoring the incisions to their original positions, they were closed up with a needle and nylon thread. To prevent post-surgical infection, an antibiotic ointment was applied.

4. Histological Observation

Animals were harvested at 2 and 4 weeks after implantation, and the implants were extracted as a single piece. The samples were immobilized by immersion for 24 hours in 10 percent neutral buffer formalin solution. Following demineralization with 10 percent formic acid-citric acid, the samples were encased in paraffin and continuous sections 4 micrometers in thickness were prepared. The sections were dyed with hematoxylin-eosin (H-E) and histologically observed by optical microscopy.

Results

FIG. 19 shows the histological observation results (at 2 weeks). The implants were enveloped in fibrous membranes. The DDM exhibited a dense structure. Multiple dentinal tubes were observed. There was extremely light infiltration by inflammatory cells.

Figure 20:
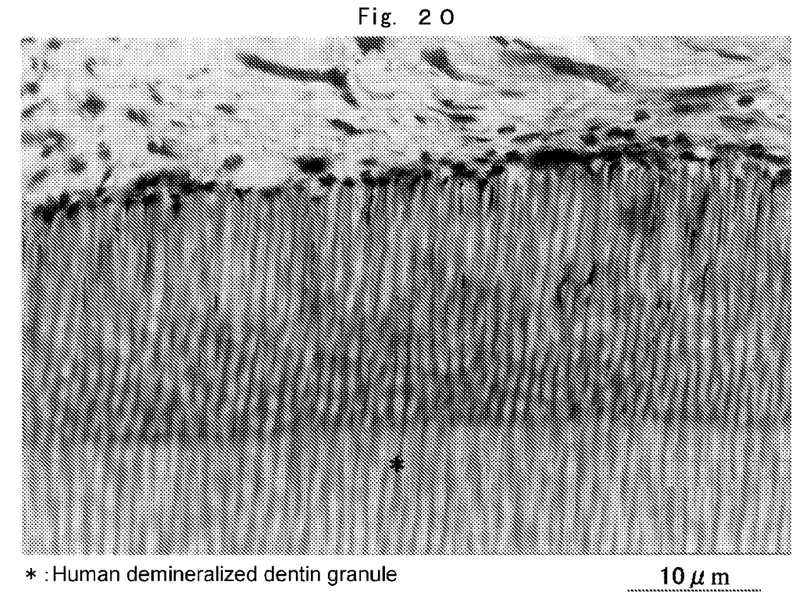
FIG. 20 Histological observation results (at 2 weeks) obtained in Embodiment 11.
Figure 21:
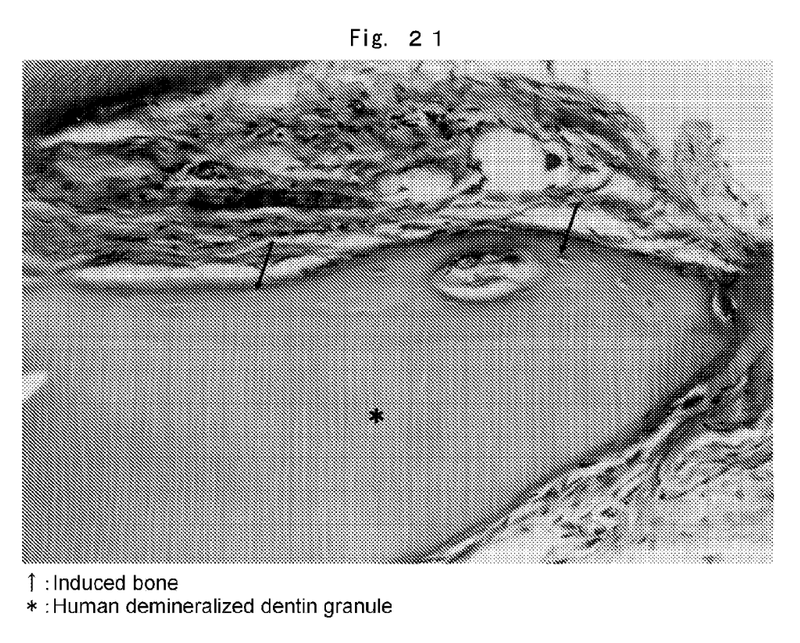
FIG. 21 Histological observation results (at 4 weeks) obtained in Embodiment 11.

FIG. 20 shows the histological observation results (at 4 weeks). Osteoinduction was recognized on the TOC-BMP granule surfaces. Resorption cavities due to polynucleomegalocytes were observed in a portion of the outer layer of the TOC-BMP, but the entire TOC-BMP remained. There was no infection or rejection of the TOC-BMP.

INDUSTRIAL APPLICABILITY

The present invention provides various kinds of materials such as an pulverized product of extracted tooth that are useful dental materials in the dental treatment of periodontal disease and the like.

The invention claimed is:

1. A method for preparing a pulverized product of an extracted tooth, the method comprising pulverizing the extracted tooth with a pulverizing apparatus to obtain a pulverized product of an extracted tooth, characterized in that:

said pulverizing apparatus comprises a sealable pulverizing chamber and a freely rotating pulverizing blade having a pulverizing surface that collides with the extracted tooth within said pulverizing chamber for a pulverizing period to pulverize the extracted tooth, wherein at least an inner wall of said pulverizing chamber and said pulverizing blade are comprised of zirconia, and an extracted tooth is pulverized by said pulverizing apparatus together with pieces of physiological saline ice without liquefied nitrogen to obtain the pulverized product of the extracted tooth, wherein a total quantity of pieces of physiological saline for a single extracted tooth falls within a range of 10 to 40; and the pulverization period is selected so that the particle size of the pulverized product of extracted tooth falls within a range of 0.1 to 2.0 mm while avoiding denaturation of the extracted tooth and contamination of materials other than zirconia.

2. The method of claim 1, wherein the rotational speed of said pulverizing blade falls within a range of 10,000 to 15,000 rpm.

3. The method of claim 1, wherein each of said pieces of physiological saline ice has a volume falling within a range of 0.5 to 8 cm$^3$.

4. The method of claim 1, wherein a single extracted tooth is pulverized in a single pulverizing cycle.

5. The method of claim 1, wherein a total quantity of pieces of physiological saline ice falling within a range of 10 to 40 cm$^3$ is employed for a single extracted tooth.

6. The method of claim 1, wherein an extracted tooth is pulverized as is to obtain a pulverized product of an extracted tooth in the form of a mixture of enamel and dentin.

7. The method of claim 1, wherein the outer surface of said extracted tooth is eliminated prior to pulverizing to obtain a pulverized product of an extracted tooth that is dentin.

8. The method of claim 1, wherein said extracted tooth is optionally washed and then said extracted tooth is pulverized as is by said pulverizing apparatus.

9. A method for preparing a pulverized product of an extracted tooth, the method comprising:

pulverizing the extracted tooth with a pulverizing apparatus to obtain a pulverized product of an extracted tooth, wherein said pulverizing apparatus comprises a sealable pulverizing chamber and a pulverizing blade having a pulverizing surface;

freely rotating the pulverizing blade having a pulverizing surface such that it collides with the extracted tooth within said pulverizing chamber for a pulverizing period to pulverize the extracted tooth, wherein at least an inner wall of said pulverizing chamber and said pulverizing blade are comprised of zirconia;

pulverizing said extracted tooth by said pulverizing apparatus together with pieces of physiological saline ice to obtain the pulverized product of the extracted tooth, wherein a total quantity of pieces of physiological saline for a single extracted tooth falls within a range of 10 to 40; and selecting the pulverization period so that the particle size of the pulverized product of extracted tooth falls within a range of 0.1 to 2.0 mm while avoiding denaturation of the extracted tooth and contamination of materials other than zirconia.

10. The method of claim 9, wherein said extracted tooth is optionally washed and then said extracted tooth is pulverized as is by said pulverizing apparatus.

* * * * *